United States Patent [19]

Collins et al.

[11] 3,972,908

[45] Aug. 3, 1976

[54] ORGANOTIN COMPOUNDS

[75] Inventors: John Desmond Collins, Albrighton; Harold Coates, Wombourn; Iftikhar Hussain Siddiqui, Birmingham, all of England

[73] Assignee: Albright & Wilson Limited, Oldbury, England

[22] Filed: Dec. 5, 1974

[21] Appl. No.: 529,799

Related U.S. Application Data

[62] Division of Ser. No. 418,591, Nov. 22, 1973, Pat. No. 3,894,989.

[30] Foreign Application Priority Data

Nov. 29, 1972 United Kingdom ............... 55042/72

Sept. 10, 1973 United Kingdom ............... 42451/73

[52] U.S. Cl. ....................... 260/429.7; 260/45.75 J; 260/45.75 S

[51] Int. Cl.[2] ........................................... C07F 7/22

[58] Field of Search .................. 260/429.7, 45.75 J, 260/45.75 S

[56] References Cited

UNITED STATES PATENTS

| | | | |
|---|---|---|---|
| 3,078,290 | 2/1963 | Hechenbleikner et al. | 260/429.7 |
| 3,196,129 | 7/1965 | Hechenbleikner et al. | 260/429.7 X |
| 3,209,017 | 9/1965 | Hechenbleikner et al. | 260/429.7 |
| 3,217,004 | 11/1965 | Hechenbleikner et al. | 260/429.7 |

*Primary Examiner*—Helen M. S. Sneed

[57] ABSTRACT

Organotin compounds of formula

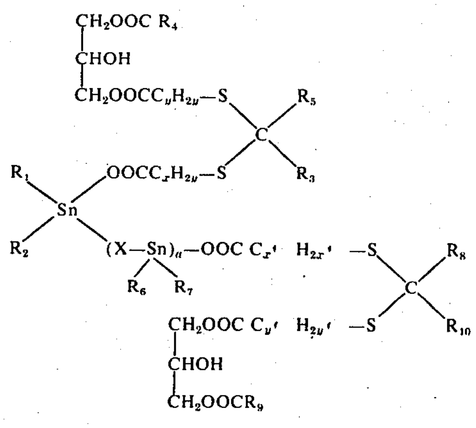

where $a$ is 0 or 1, $x$, $x'$, $y$ and $y'$ are 1–6, $R_1$, $R_2$ $R_6$ and $R_7$ are $C_{1-12}$ alkyl, cycloalkyl, aromatic or aralkyl hydrocarbyl, $R_4$ and $R_9$ are as defined for $R_1$ or are $C_{13-21}$ alkyl, $C_{2-21}$ alkenyl or substituted aromatic hydrocarbyl, $R_3$, $R_5$, $R_8$ and $R_{10}$ are as defined for $R_4$ or are hydrogen or a pair of $R_3$ and $R_5$ or $R_8$ together with the carbon atom to which they are joined forms a cycloalkyl ring and X is O or S, are stabilizers for halogen containing resins, especially PVC.

26 Claims, No Drawings

ORGANOTIN COMPOUNDS

This is a divisional of application Ser. No. 418,591, filed Nov. 22, 1973, now U.S. Pat. No. 3,894,989.

The present invention relates to organotin compounds and to their use as stabilizers for polymeric materials, in particular halogenated resins such as polymers and copolymers of vinyl chloride and vinylidene chloride.

The use of organotin compounds containing sulphur as stabilizers for halogenated resins has for many years been recognised as being highly effective. However, the compounds employed have normally been those having a comparatively high tin content and so, in view of the high cost of tin, are expensive relative to other available stabilisers. Thus, despite their high efficiency these compounds are still not as widely used as other, less effective, materials.

The compounds of the present invention are sulphur-containing organotin compounds which have a lower tin content than most conventional sulphur-containing organotin compounds and so are potentially cheaper.

Accordingly, the present invention provides new chemical compounds of the formula:

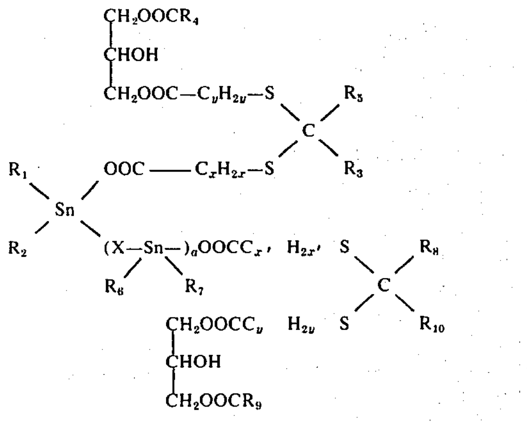

I wherein

- $a$ is 0 or 1, each of $R_1$, $R_2$, $R_6$ and $R_7$, which are the same or different, is an alkyl group of 1 to 12 carbon atoms, cycloalkyl group, aromatic hydrocarbyl group e.g. of 6 to 19 carbon atoms e.g. phenyl or aralkyl hydrocarbyl group e.g. of 7 to 19 carbon atoms such as benzyl,
- each of $R_4$ and $R_9$, which are the same or different, is as defined above for $R_1$, $R_2$, $R_6$ and $R_7$ or is an alkyl group of 13–21 carbon atoms, an alkenyl group of 2-21 carbon atoms or an inertly substituted aromatic hydrocarbon group, wherein the substituent is preferably at least one group of formula —OH, —$OR_4$, —$SR_4$, —$COOR_4$, —$OOCR_4$ or —$SSR_4$,
- each of $R_3$, $R_5$, $R_8$ and $R_{10}$, which are the same or different, is as defined above for $R_4$ and $R_9$, or is hydrogen or at least one of the pairs $R_3$ and $R_5$, and $R_8$ and $R_{10}$ together with the carbon atom to which they are attached forms a cyclo alkyl ring, preferably a cyclohexane ring,
- each of $x$, $x'$, $y$ and $y'$, which are the same or different is an integer of 1–6, and X is oxygen or sulphur.

Preferably the compounds are symmetric with $R_1$, $R_2$, $R_3$, $R_4$, $R_5$, $x$ and $y$ the same respectively as $R_6$, $R_7$, $R_8$, $R_9$, $R_{10}$, x' and y'. $R_1$, $R_2$, $R_6$ and $R_7$ are preferably $C_4$ to $C_8$ alkyl e.g. n-butyl or n-octyl groups or cycloalkyl groups of 5–7 carbon atoms e.g. cyclohexyl groups. $R_5$ and $R_{10}$ are preferably hydrogen or alkyl of 1 to 6 carbon atoms e.g. methyl groups. $R_4$ and $R_9$ are normally alkyl or alkenyl groups of 10 to 19 carbon atoms, preferably linear ones e.g. of formula $CH_3(CH_2)_z$ —, where $z$ is an integer of 9–18, preferably 10–16 and especially 17. $R_3$ and $R_8$ are preferably phenyl or substituted phenyl (the substituents being for example alkyl of 1 to 6 carbon atoms especially methyl, or alkoxy of 1 to 6 carbon atoms, especially methoxy or hydroxy) groups, branched chain alkyl group of 3–10 preferably 4–8 carbon atoms preferably those in which the free valency is at the point of branching i.e. of formula —CH $R_{11}$ $R_{12}$, where $R_{11}$ and $R_{12}$ are alkyl groups of 1 to 6 carbon atoms especially ethyl and butyl e.g. pent-3-yl and hept-3-yl groups or straight chain alkyl groups of 7 to 13 carbon atoms e.g. n-nonyl and n-undecyl groups. $x$ and $x'$ are preferably 1 or 2, $y$ and $y'$ are preferably 1 or 2, and X is preferably oxygen. The groups $C_xH_{2x}$, $C_{x'}H_{2x'}$, $C_yH_{2y}$ and $C_{y'}H_{2y'}$ are preferably linear e.g. of formula $(CH_2)_x$.

In preferred compounds of formula I, the groups

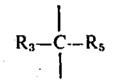

and

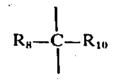

are the same and represent groups of formula

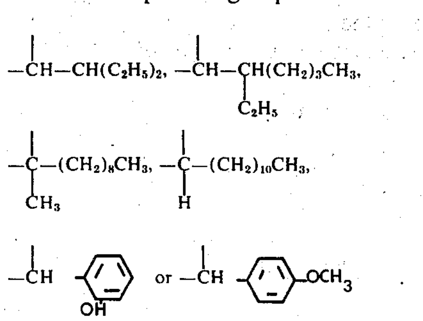

When $a$ is 0 , the compounds of the present invention are of the formula:

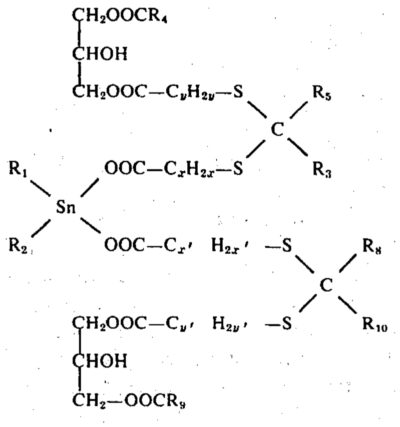

II

In the above formula II, $R_4$ and $R_9$ is preferably of formula $(CH_2)_zR_{13}$, $R_3$, $R_8$ and $R_{13}$ are each an alkyl group of 1 to 13 carbon atoms a cycloalkyl group, an aryl or aralkyl group, $R_5$ and $R_{10}$ are hydrogen, an alkyl or an aryl group and $z$ is an integer of 1 to 20. $R_{13}$ is most preferably a methyl group. The groups $C_x H_{2x}$, $C_{x'} H_{2x'}$, $C_yH_{2y}$ AND $C_{y'} H_{2y'}$ are preferably $(CH_2)_x$, $(CH_2)_{x'}$, $(CH_2)_y$ and $(CH_2)_{y'}$.

When $a$ is 1, the compounds of the present invention are of the formula:

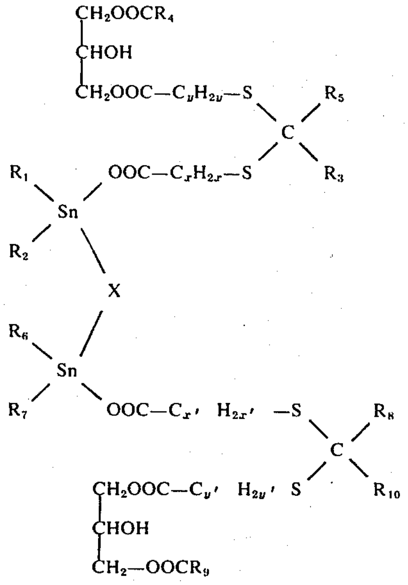

III

In a second aspect the invention provides a process for preparing the compounds of the invention by reacting at least one precursor of formula IV

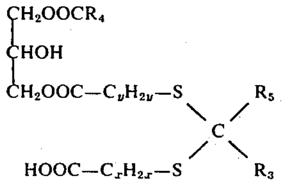

IV or formula V

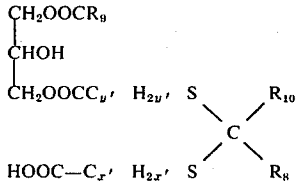

V with at least one tin compound of formula $R_1R_2SnO$, $R_6R_7SnO$, $R_1 R_2 SnS$ or $R_6 R_7 SnS$, If the ratio of the total number of moles of tin compound to the total number of moles of precursors is at least 1:1, then compounds of formula III are formed. If the ratio of the total number of moles of tin compound to the total number of moles of precursors is 0.5 : 1 or less than compounds of formula I, wherein $a$ is 0 (i.e. of formula II) are formed. When the ratio is between 0.5:1 and 1:1 both compounds of formula II and III are formed.

The process can be carried out in several different ways. Thus to prepare the symmetrical compounds of formula III, one mole of a precursor of formula IV can be reacted directly with at least one mole of tin compound of formula $R_1R_2$ SnO (when X in the compound of formula I is oxygen) or at least one mole of tin compound of formula $R_1R_2SnS$ (when X in the compound of formula I is sulphur).

To prepare the symmetrical compounds of formula II one mole of precursor can be reacted with 0.5 mole of tin compound of formula $R_1R_2Sn$ O or $R_1R_2$ SnS. These symmetrical compounds of formula II can be converted into compounds of formula III by reaction with at least 0.5 mole (per mole of the compound of formula II) of tin compound of formula $R_1R_2SnO$ (when X is to be oxygen) or $R_1R_2SnS$ (when X is to be sulphur). The compounds of formula III can be converted into those of formula II by treatment with more precursor compounds of formula IV and/or V, e.g. with an extra 0.5 mole precursor per mole of compound of formula III.

The precursors of formula IV can be prepared by reacting at least one mole of a mono ester of glycerol of formula $HOCH_2$ CHOH $CH_2OCOR_4$ with one mole of a mercapto carboxylic acid of formula HS $C_yH_{2y}$ COOH to produce an intermediate of formula HS $C_yH_{2y}$ COO $CH_2CHOH$ $CH_2OCO$ $R_4$, reacting this intermediate with a carbonyl compound of formula $R_3R_5CO$ and a mercapto carboxylic acid of formula $HSC_xH_{2x}$ COOH to produce the percursor of formula IV, the intermediate, carbonyl compound and latter mercapto carboxylic acid being used in about equimolar amounts. A corresponding sequence of reactions can be used to prepare the precursors of formula V.

To prepare asymmetric compounds of formula I, precursors of formula IV and V, which are different, are used if the asymmetry is in the part of the molecule derived from the precursors, and for compounds of formula I, where $a$ is 1, at least two organotin compounds, one containing $R_1$ and $R_2$ groups and the other different $R_6$ and $R_7$ groups, are used if the asymmetry is in the groups attached to tin.

Frequently all the reactions to form the compounds of formula I are carried out in the same solvent medium, which may be an aromatic hydrocarbon, e.g. benzene, toluene or xylene, an aliphatic hydrocarbon e.g. hexane or petroleum ether b.p. 80° or a cycloaliphatic hydrocarbon e.g. cyclohexane. It is often desirable to have an acidic catalyst present in the reaction, e.g. p-toluene sulphonic acid, hydrochloric acid or a metal chloride suitable as a Friedel Crafts catalyst, such as zinc chloride.

Examples of compounds of formula II according to the invention include:

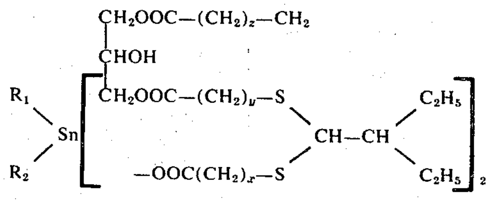

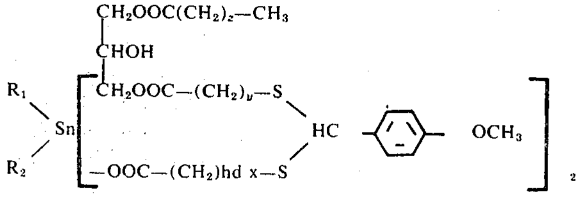

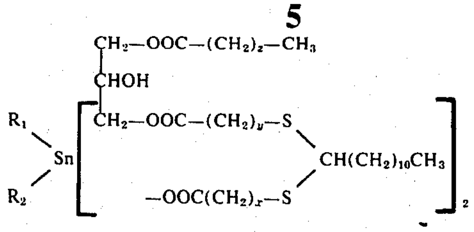
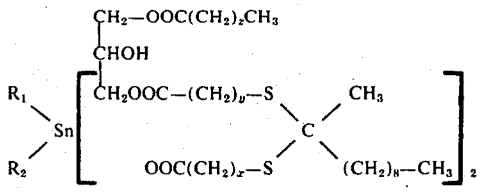
Particular compounds of formula II according to the present invention include:
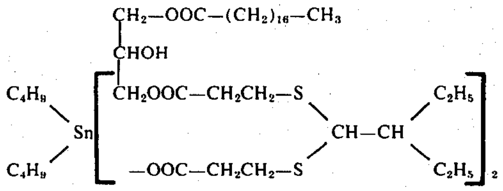
VI
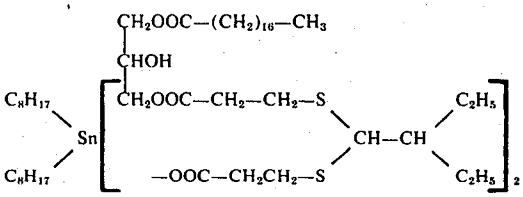
VII
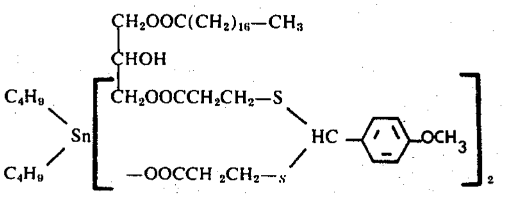
VIII
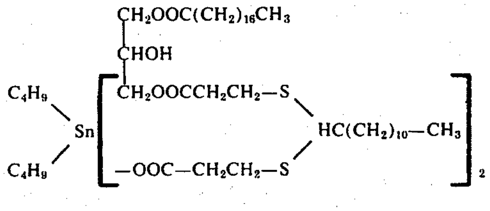
IX
Corresponding compound of formula IX with $(C_8H_{17})_2$ Sn instead of $(C_4H_9)_2$ is of formula X
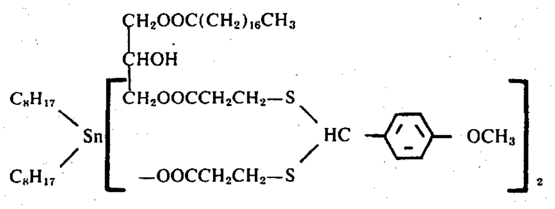
X
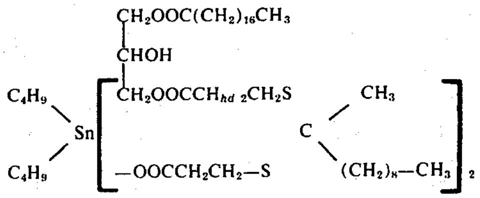
XI
Particular compounds of formula III according to the present invention include:
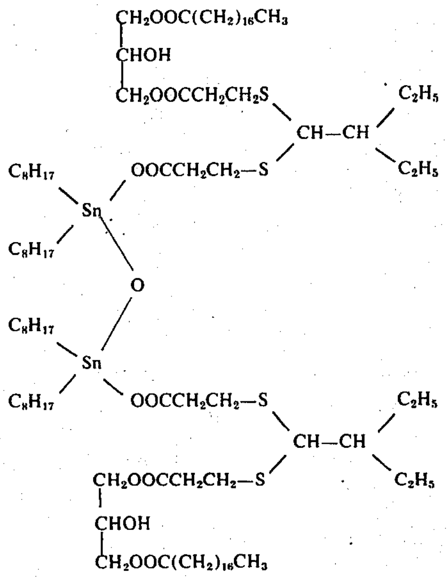
XII
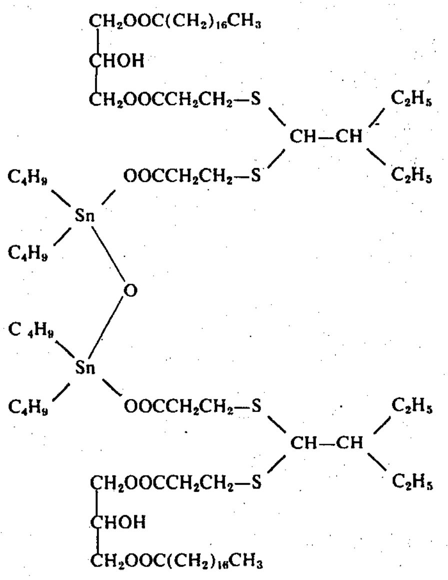
XIII
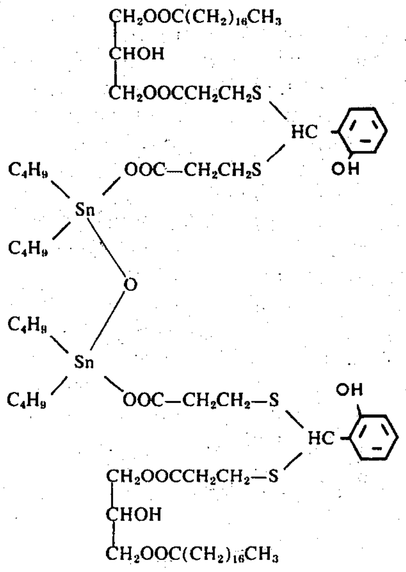
XIV -continued

XV

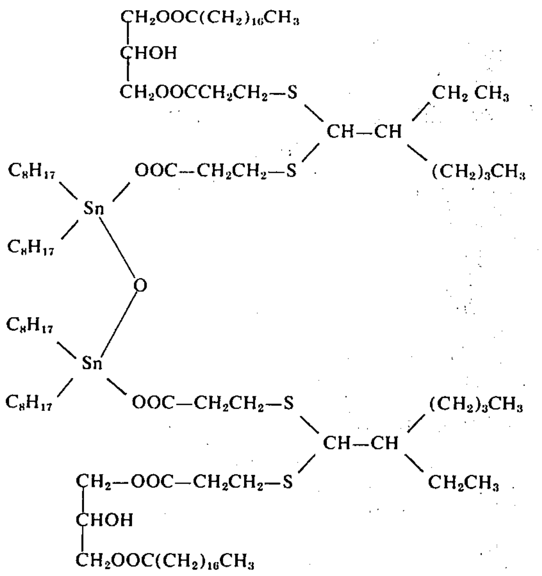

XVI

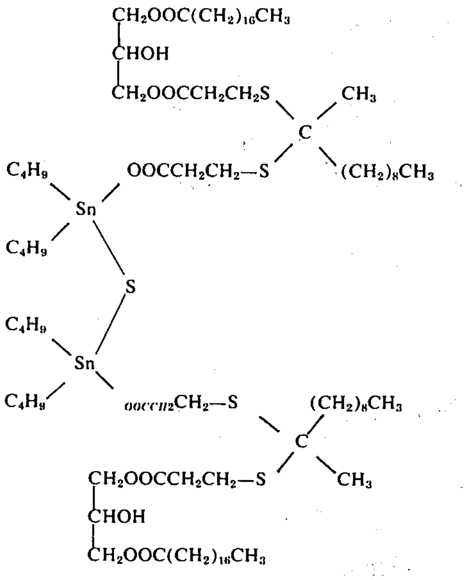

Compounds according to the invention find use as stabilisers for halogen-containing resins, that is for polymers or copolymers of vinyl chloride or vinylidene chloride, chlorinated vinyl chloride polymers and chlorinated polyethylene. Accordingly, from a further aspect the present invention provides a composition which comprises a halogen-containing resin and as a stabiliser therefore a compound of the formula I.

The organotin compounds will be present in compositions according to the invention in amounts so as to produce the desired stabilising effect; often this will be from 0.01–10%, preferably 0.2–5% and especially 2 to 3% by weight based on the total amount of polymeric resin present.

It has also been found that by mixing 1–50% by weight (based on the weight of the organotin compound of the invention) of a monoalkyltin compound such as a monoalkyltin tris (mercapto glycollate) ester of a $C_{1-20}$ alkanol e.g. monobutyltin tris (iso-octyl thioglycollate) with the organotin compound, the stabilizing efficiency of the compound increases. Preferably 5–25% based on total amount of organotin compound is used. Other additives which also improve the initial clarity of polymer during thermal tests with organotin compounds are:

a. Butyl epoxy stearate (B.E.S.)
b. Mono-octyltin tri (iso-octyl thioglycollate)
c. Dibutyltin sulphide and oxide
d. Dibutyltin cyclic mercapto acetate and/or Dibutyltin cyclic β-mercapto propionate and/or Dioctyltin cyclic mercapto acetate and/or Dioctyltin cyclic β-mercapto propionate.

Optionally, but advantageously, compositions according to the invention also contain hindered phenols, that is those having at least one alkyl substituent in a position ortho to the hydroxyl group, as auxiliary stabilisers. Such phenols preferably have 1–8 carbon atoms in each alkyl group, which is especially a tertiary butyl group. Examples of such phenols include butylated hydroxy-anisole, 2,6di-tert.-butylphenol, butylphenol, methylene bis-(2,4-di-tert.-butylphenol), methylene bis-(2,6-di-tert.-butylphenol), methylene bis-(2,6-di-tert.-butyl-3-methylphenol), 4,4'-butylidene bis-(6-tert.-butyl-3-methylphenol), methylene bis-(4-ethyl-6-tert.-butylphenol), methylene bis-(4-methyl-2,6-di-tert.-butylphenol). Particularly preferred, however, is 2,6-di-tert,-butyl-4-methyl-phenol.

Such phenols may be present in an amount of up to 3% preferably from 0.01 to 0.05% by weight of the resin and will normally be present at about 4–10% by weight, preferably 5–8% based on the total amount of organotin compounds used.

Esters of phosphorous and thiophosphorous acid may be employed in compositions according to the invention. Such compounds include halo-phosphites such as tris chloropropyl phosphite and polymeric phosphites such as those from hydrogenated 44'-isopropylidene diphenol. Preferred phosphites and thiophosphites, however, are monomers having no substituents in the organo-group and having no more than one sulphur atom. These include triaryl phosphites and trialkyl phosphites. Such compounds include, for example, triphenyl phosphite, trixylyl-phosphite, trinonyl phenyl phosphite and trioctyl phosphite. Diesters of phosphorous acid such as di-isopropyl phosphite, dibutyl phosphite and diphenyl phosphite are also of use. Particularly preferred, however, are the mixed alkyl aryl phosphites such as octyl diphenyl phosphite, isodecyl diphenyl phosphite and diisodecyl phenyl phosphite. This particularly pronounced effect may also be obtained by employing a mixture of a triaryl phosphite and an alcohol in conjunction with the organotin compound. A particularly suitable mixture is that of triphenyl phosphite and isodecanol.

The stabiliser composition of the invention can also contain an epoxy compound, as may be desired for example in cases where a delay of initial colour change of the polymer is desired. Epoxy compounds which may be employed in such compositions include butyl epoxy stearate, esters of epoxidised oleic acid and compounds of the formula

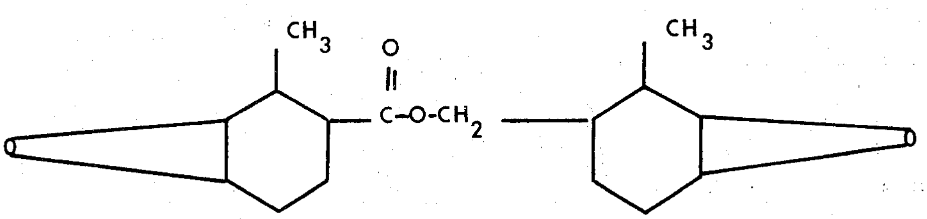

Organotin formulations as described above, optionally including a hindered phenol, an alkyl aryl phosphite or aryl phosphite or an epoxide, will often be used as the only stabiliser in a polymeric vinyl chloride or vinylidene chloride compositions. However, if desired conventional thermal stabilizers may also be included. These may include, for example, metal soap stabilisers, such as cadmium, barium, or zinc salts of fatty acids, or lead salts such as lead carbonate or stearate or dibasic lead phosphite or phthalate, or tribasic lead sulphate or conventional organotin stabilisers such as dibutyltin dilaurate or dibutyltin maleate or sulphur-containing compounds such as dibutyltin bisthioglycollates.

In the practice of the invention the stabiliser formulation may be mixed with the copolymer resin in the conventional manner for example by milling with the resin on heated rolls at 100°–160°C e.g. about 150°c., although higher temperatures may be used when convenient, or by being mixed with particles of the polymer and then melting and extruding the mixture or by adding the stabiliser to a liquid resin.

Resins which may be used in compositions according to the invention normally contain at least 40% by weight of chlorine. Usually it will be a polymer or copolymer of vinyl chloride or or vinylidene chloride but post-halogenated polyvinyl chloride or post-halogenated polyolefines, such as polyethylene, may be employed if desired. Suitable monomers which may form such copolymers with vinyl chloride and vinylidene chloride include for example acrylonitrile, vinyl acetate, methyl methacrylate, diesters of fumaric acid and maleic acid, ethylene, propylene and lauryl vinyl ether and these co-monomers may be present in an amount of up to 25% of the total weight of monomers copolymerised.

The organotin stabiliser formulation may be employed in either plasticised resin compositions, for example those plasticised with carboxylic ester plasticisers e.g. di-2-ethylhexyl phthalate, dibutyl sebacate or di-isooctyl phthalate or with phosphate esters such as tri(alkyl phenyl) phosphates or may be employed in rigid compositions. Such rigid compositions contain little or no plasticisers although for some applications up to about 10% by weight of plasticiser may be present. This is in contrast with plasticised compositions where the amount of plasticisers present is normally greater than 50% by weight of the polymeric material and is often greater than 100% on that basis; amounts of 30 – 150% are often used.

In addition to the stabilizers, the compositions of the invention may also contain conventional additives e.g. pigments, fillers, dyes and ultraviolet absorbing agents, The invention is illustrated in the following Examples:

EXAMPLE 1

Preparation of Compound of Formula VI

Glycerol mono stearate (34.8g, 0.1M) and β-mercaptopropionic acid (10.6g, 0.1M) were refluxed in toluene (250 ml) in presence of p-toluene sulphonic acid (ca. 0.2g–0.3g) till the calculated amount of water had collected [to give $C_{17}H_{35}COOCH_2-CH(OH)-CH_2OOC-CH_2CH_2\ SH$.]

2-ethyl butyraldehyde (10.0g, 0.1M) and β-mercaptopropionic acid (10.6g, 0.1M) were also added into the above warm solution and the mixture refluxed until the calculated amount of water had collected again $$C_2H_5-CH-C_2H_5$$

$$[\text{to give } C_{17}H_{35}COOCH_2-CH(OH)-CH_2OOCCH_2CH_2S-CH-SCH_2CH_2COOH]$$

After cooling the solution dibutyltin oxide (12.5g, 0.05M) was added to the solution and the mixture refluxed until a clear solution was obtained. The hot solution was thus filtered under vacuum and finally the toluene was removed from the warm solution under reduced pressure.

The product is a white soft waxy solid at room temperature.

| Analysis Calculated | Found |
|---|---|
| Sn = 7.9% | Sn = 8.07% |
| S = 8.5% | S = 8.69% |

Its structure was also confirmed by I.R. & N.M.R.

EXAMPLE 2

Preparation of Compound of Formula VII

This compound was prepared by the same method as in Example 1 using the following quantities:

| | | |
|---|---|---|
| Step (1) | (a) Glycerol mono stearate | 34.8g |
| | (b) β-Mercaptopropionic acid | 10.6g |
| | (c) p-toluene sulphonic acid | ca.0.2 g |
| | (d) toluene | 250 ml |
| Step (2) | (e) 2-ethyl butyraldehyde | 10 g |
| | (f) β-mercaptopropionic acid | 10.6 g |
| Step (3) | (g) Dioctyltin oxide | 18.1 g |

The product is a white soft waxy-like solid at room temperature.

| Analysis Calculated | Found |
|---|---|
| Sn = 7.37% | Sn = 6.4% |
| S = 7.9 % | S = 8.4% |

Its structure was also confirmed by I.R. and N.M.R.

EXAMPLE 3

Preparation of Compound of formula VIII

It was prepared by the same method as in Example 1 using the following quantities:

It was prepared by the same method as in Example 1 using the following quantities:

| | | |
|---|---|---|
| Step (1) | (a) Glycerol mono stearate | 34.8 g |
| | (b) β-Mercaptopropionic acid | 10.6 g |
| | (c) p-toluene sulphonic acid | ca.0.3g |
| | (d) Toluene | 300 ml |
| Step (2) | (e) Anisaldehyde | 13.6 g |
| | (f) β-mercaptopropinic acid | 10.6 g |
| Step (3) | (g) Dibutyltin oxide | 12.5 g |

The product is a slightly yellow, soft wax-like solid at room temperature.

| Analysis Calculated | Found |
|---|---|
| Sn = 7.55% | Sn = 7.4% |
| S = 8.14% | S = 7.5% |

Its structure was also confirmed by I.R. and N.M.R.

EXAMPLE 4

Preparation of compound of formula X

It was prepared by the same method as in Example 1 using the following quantities:

| | | |
|---|---|---|
| Step (1) | (a) glycerol mono stearate | 34.8 g |
| | (b) β-mercaptopropionic acid | 10.6 g |
| | (c) p-toluene sulphonic acid | ca.0.2g |
| | (d) toluene | 300 ml |
| Step (2) | (e) dodecylaldehyde | 18.4 g |
| | (f) β-mercaptopropionic acid | 10.6 g |
| Step (3) | (g) dioctyltin oxide | 18.0 g |

The product is a white soft wax - like solid at room temperature.

| Analysis Calculated | Found |
|---|---|
| Sn = 6.7% | Sn = 6.3% |
| S = 7.1% | S = 6.7% |
| C = 63.4% | C = 62.54% |
| H = 10.1% | H = 10.52% |

Its structure was also confirmed by I.R.

EXAMPLE 5

Preparation of compound of Formula IX

It was prepared exactly by the same method and using the same quantities of starting materials as in Example 4, with the difference in step (3) i.e. using dibutyltin oxide (12.5g) instead of dioctyltin oxide.

The product is a white soft wax-like solid at room temperature.

-continued

| Analysis Calculated | Found |
|---|---|
| Sn = 7.12% | Sn = 7.0% |
| S = 7.67% | S = 7.4% |

EXAMPLE 6

Preparation of compound of formula XI

It was prepared exactly by the same method and using the same quantities of starting materials as in Example (1), with the difference in step (2) i.e. using Methyl Nonyl ketone (17g 0.1M) instead of 2-Ethyl Butyraldehyde.

The product is a white soft wax-like solid at room temperature.

| Analysis Calculated | Found |
|---|---|
| Sn 7.24% | 6.76% |
| S 7.8% | 7.25% |
| C 61.5% | 60.5 |
| H 9.7% | 9.83% |

The structure was also confirmed by I.R. and N.M.R. analysis.

EXAMPLE 7

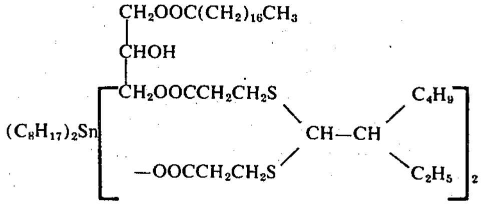

This compound was prepared by the same method as in Example 1 but using the following materials and quantities.

| | | |
|---|---|---|
| Step (1) | (a) glycerol monostearate | 69.6 g |
| | (b) β-mercaptopropionic acid | 21.2 g |
| | (c) p-toluene sulphonic acid | ca 0.3 g |
| | (d) Toluene | 200 ml |
| Step (2) | (e) β-mercaptopropionic acid | 21.2 g |
| | (f) 2-ethyl hexanol | 25.6 g |
| Step (3) | (g) Dioctyltin oxide | 36.1 g |

The product is a white waxy solid at room temperature, whose structure was confirmed by its infra red and n m r spectra.

| Analysis Calculated | Found |
|---|---|
| Sn 7.1% | 7.0% |
| S 7.6% | 8.0% |
| C 61.9% | 61.1% |
| H 9.95% | 9.96% |

EXAMPLE 8

Preparation of compound of formula XIII

The final hot solution obtained in Example 1 and containing the compound of formula VI was cooled, dibutyltin oxide (12.5g, 0.05M) was added thereto and the mixture refluxed until a clear solution was obtained. The hot solution was then filtered under vacuum and finally the toluene was removed from the warm solution under reduced pressure to leave the product as a white soft waxy solid at room temperature.

| Analysis Calculated | Found |
|---|---|
| Sn = 13.5% | Sn = 12.65% |
| S = 7.3% | S = 7.3% |
| C = 56.2% | C = 55.01% |
| H = 9.03% | H = 8.77% |

Its structure was also confirmed by I.R. and N.M.R.

EXAMPLE 9

Preparation of compound of formula XII

This compound was prepared by heating the final solution obtained by the method of Example 2 and containing the compound of formula VII(32.2g. 0.02 M) and dioctyltin oxide (7.2 gms, 0.02 M) with constant stirring and heating to reflux till a clear solution was obtained. The product was isolated as described in Example 8. The product is a white soft waxy solid at room temperature.

| Analysis Calculated | Found |
|---|---|
| Sn% = 12.0 | Sn% = 11.5 |
| S% = 6.4 | S% = 6.9 |
| C% = 60.7 | C% = 61.79 |
| H% = 9.6 | H% = 9.65 |

Its structure was also confirmed by I.R. and N.M.R. analysis.

EXAMPLE 10

Preparation of compound of formula XIV

This compound was prepared by the same method as in Example 8 using the following quantities:

| | | |
|---|---|---|
| Step (1) | (a) Glycerol monostearate | 34.8 g. |
| | (b) β-Mercaptopropionic acid | 10.6 g. |
| | (c) p-toluene sulphonic acid | Ca. 0.2 g. |
| | (d) toluene | 200 ml. |
| Step (2) | (e) Salicylaldehyde | 12.2 g. |
| | (f) β-mercaptopropionic acid | 10.6 g. |
| Step (3) | (g) dibutyltin oxide | 12.5 g. |
| Step (4) | (h) dibutyltin oxide | 12.5 g. |

The product is a slightly yellow waxy solid at room temperature.

| Analysis Calculated | Found |
|---|---|
| Sn = 13.2% | = 12.2% |
| S = 7.1% | S = 7.3% |

Its structure was also confirmed by I.R. and N.M.R.

EXAMPLE 11

Preparation of compound of formula XV

This compound was prepared by the same method as in Example 9 i.e. by heating dioxtyltin oxide (10.8g., 0.03M) and the final solution obtained by the method of Example 7 and containing

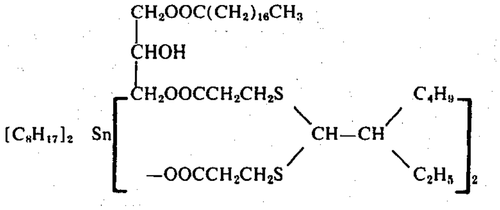

(50 g., 0.3 M) with constant stirring and heating to reflux till a clear solution was obtained.

The product is a slightly yellow coloured solid at room temperature.

| Analysis Calculated | Found |
|---|---|
| Sn = 11.7% | Sn = 11.4% |
| S = 6.3% | S = 7.0% |
| C = 60.3% | C = 60.5% |
| H = 9.7% | H = 9.9% |

EXAMPLE 12

Preparation of compound of formula XVI

This compound was prepared by the same method as in Example 11 by heating dibutyltin sulphide (5.3g, 0.02 M) and the final solution obtained by the method of Example 6 and containing the compound of formula XI (32.8g, 0.02 M) with constant stirring till a clear solution was obtained.

The product is a white waxy solid at room temperature.

| Analysis Found % | Calculated % |
|---|---|
| Sn = 11.75 | Sn = 12.4 |
| S = 7.6 | S = 8.4 |
| C = 57.9 | C = 58.0 |
| H = 9.8 | H = 9.3 |

EXAMPLE 13

Polyvinyl chloride resins containing compounds of Examples 1–7 and 8–12 were tested for initial colour development against known stabilisers (with and without mono-butyltin tri iso-octyl thioglycollate) on an equal tin basis for Examples 1–6 (Table 1) and on an equal part basis for Examples 8–12 (Table 2). Improved results were obtained in spite of the lower tin content of the compounds of the invention as compared to the known stabilizers (see Tables 1 and 2).

The known stabilizers were dibutyltin bis(iso-octyl) thiioglycollate) and dioctyltin bis (iso-octyl thioglycollate) with and without monobutyltin tri(iso-octyl thioglycollate).

A series of rigid (non-plasticized) formulations was prepared from the polyvinyl chloride resin Corvic D55/09 (100 Parts). When testing the compounds of the invention lubricant has not been added added to the polymer because the new compounds tested themselves act as a lubricant during milling at about 155°C, but with known stabilizers 0.5 parts of Lubricant (Laurex $C_S$) per 100 parts of Polymer) has been added (marked * in Tables 1 and 2). In some cases monobutyltin tri(iso octyl thioglycollate) has also been added (marked A in Table 2). Laurex CS is the trade name for a mixture of cetyl and stearyl alcohols.

Table 1

Testing of stabilisers (with and/or without additives) in comparison with known stabilisers containing equal amount of tin in Polyvinyl chloride.

| Test | Stabilizer(s) | Parts of stabiliser(s) in 100 parts of PVC | Colour on Gardner scale after heating at 190°C for given time in min. 0 | 5 | 10 | 15 |
|---|---|---|---|---|---|---|
| 1 | (a) Product Ex 1 | (a) 1.5 | 0 | 0 | 3+ | — |
| | (b) *DBT(IOT)$_2$ | (b) Tin equivalent to (a) | 2+ | 5+ | 8 | — |
| 2 | (a) Product Ex 4 | (a) 1.5 part | 0+ | 2+ | 9 | — |
| | (b) *DOT(IOT)$_2$ | (b) Tin equivalent to (a) | 5 | 6 | — | — |
| 3 | (a) Product Ex 3 | (a) 2.0 part | 1 | 3 | 4 | — |
| | (b) *DBT(IOT)$_2$ | (b) Tin equivalent to (a) | 0 | 3+ | 7 | — |
| 4 | (a) Product Ex 5 | (a) 1.5 part | 1 | 3 | — | — |
| | (b) *DBT(IOT)$_2$ | (b) Tin equivalent to a | 1 | 5 | — | — |
| 5 | (a) Product Ex 2 | (a) 1.5 part | 0 | 0 | 2 | 4 |
| | (b) *DBT(IOT)$_2$ | (b) Tin equivalent to 2 | 3+ | 5 | 9 | 9 |
| 5(a) | (a) Prod. Ex 6 | (a) 1.5 parts | 0 | 0 | 1 | 5 |
| | (b) *DBT(IOT)$_2$ | (b) Tin equivalent to (a) | 1 | 5 | 8 | |
| 6 | (a) *DBT(IOT)$_2$ | (a) 0.3 | 4 | 5–6 | — | — |
| | (b) Product Ex 1 | (b) Tin equivalent to (a) | 0 | 1 | — | — |
| 7 | (a) *DBT(IOT)$_2$ | (a) 0.5 | 2 | 4 | 8 | — |
| | (b) Product Ex 1 | (b) Tin equivalent to (a) | 0 | 1 | 3 | — |
| 8 | (a) *DBT(IOT)$_2$ | (a) 0.8 | 1 | 4 | 6 | 7–8 |
| | (b) Product Ex 1 | (b) Tin equivalent to (a) | 0 | 0–1 | 2 | 4 |
| 9 | (a) *DBT(IOT)$_2$ | (a) 0.166 | 7 | 9 | — | — |
| | (b) Product Ex 1 | (b) Tin equivalent to (a) | 0 | 2–3 | — | — |
| 10 | (a) *DOT(IOT)$_2$ | (a) 0.75 | 3 | 5 | 8 | 9 |
| | (b) Product Ex 2 | (b) Tin equivalent to (a) | 0 | 0 | 2 | 5 |
| 11 | (a) *DOT(IOT)$_2$ | (a) 0.5 | 6 | 7 | 9 | — |
| | (b) Product Ex 2 | (b) Tin equivalent to (a) | 0 | 0 | 3 | — |
| 12 | (a) *DOT(IOT)$_2$ | (a) 0.3 | 6 | 8 | — | — |
| | (b) Product Ex 2 | (b) Tin equivalent to (a) | 0 | 1 | — | — |
| 13 | (a) *DBT(IOT)$_2$ | 1.0 | 3 | 4 | 5 | |
| | (b) Product Ex 8 | 1.0 | 0 | 0 | 1–2 | |
| | (c) Product Ex 8 | 0.9 | 0 | 0 | 1–2 | |
| | (d) Product Ex 8 | 0.8 | 0 | 0 | 2 | |
| | (e) Product Ex 8 | 0.7 | 0 | 0 | 3 | |
| 13(a) | (a) DOT(IOT)$_2$ | 1.0 | 0 | 1 | 4 | |
| | (b) Product Ex 7 | 0.75 | 0–1 | 2 | 8 | |
| 14 | (a) *DBT(IOT)$_2$ | 1.0 | 3 | 4 | 5–6 | |
| | (b) Product Ex 8 | 1.0 | 0 | 0 | 1–2 | |
| | (c) *DBT(IOT)$_2$(95)+A(5) | 1.0 | 2 | 3 | 5–6 | |
| | (d) Product Ex 8(95)+A(5) | 1.0 | 0 | 0 | 1–2 | |
| | (e) *DBT(IOT)$_2$(90)+A(10) | 1.0 | 0–1 | 2 | 5 | |
| | (f) Product Ex 8(90+A(10) | 1.0 | 0 | 0 | 1–2 | |
| 15 | (a) *DBT(IOT)$_2$ | 1.0 | 2 | 3 | 4–5 | |
| | (b) Product Ex 8 | 1.0 | 0 | 0 | 1–2 | |
| | (c) *DBT(IOT)$_2$(85)+A(15) | 1.0 | 0–1 | 1–2 | 4 | |
| | (d) Product Ex 8(85)+A(15) | 1.0 | 0 | 0 | 1 | |
| | (e) *DBT(IOT)$_2$(80)+A(20) | 1.0 | 0 | 1 | 4 | |
| | (f) Product Ex 8 (80)+A(20) | 1.0 | 0 | 0 | 1 | |
| 16 | (a) *DBT(IOT)$_2$ | 1.0 | 2 | 3 | 4–5 | |
| | (b) Product Ex 8 | 1.0 | 0 | 0 | 1–2 | |
| | (c) *DBT(IOT)$_2$(75)+A(25) | 1.0 | 0 | 1 | 2–3 | |
| | (d) *DBT(IOT)$_2$(70)+A(30) | 1.0 | 0 | 0 | 2–3 | |
| | (e) *DBT(IOT)$_2$(65)+A(35) | 1.0 | 0 | 0 | 2–3 | |
| | (f) *DBT(IOT)$_2$(60)+A(40) | 1.0 | 0 | 0 | 2–3 | |
| 17 | (a) *DOT(IOT)$_2$ | 1.0 | 0 | 2 | 4–5 | |
| | (b) Product Ex 9 | 1.0 | 0 | 0 | 2 | |
| 18 | (a) *DOT(IOT)$_2$ | 1.5 | 0 | 1–2 | 4 | |
| | (b) Product Ex 9 | 1.5 | 0 | 0 | 2 | |
| 19 | (a) *DBT(IOT)$_2$ | 1.0 | 3 | 4 | 5 | |
| | (b) *DBT(IOT)$_2$ | 1.5 | 1 | 2 | 4 | |
| | (c) Product Ex 10 | 1.5 | 0 | 0 | 1–2 | |
| | (d) Product Ex 10 | 1.0 | 0 | 0 | 1–2 | |
| | (e) Product Ex 10 | 0.6 | 0 | 0–1 | 1–2 | |

Table 1-continued

Testing of stabilisers (with and/or without additives) in comparison with known stabilisers containing equal amount of tin in Polyvinyl chloride.

| Test | Stabilizer(s) | | Parts of stabiliser(s) in 100 parts of PVC | Colour on Gardner scale after heating at 190°C for given time in min. 0 | 5 | 10 | 15 |
|---|---|---|---|---|---|---|---|
| 20 | (a) | *DOT(IOT)$_2$ | 1.0 | 3 | 4–5 | 5 | |
| | (b) | Product Ex 11 | 1.0 | 0 | 0 | 2 | |
| | (c) | Product Ex 11 | 0.8 | 0 | 0 | 2–3 | |
| | (d) | Product Ex 11 | 0.6 | 0 | 0 | 3 | |
| 21 | (a) | *DBT(IOT)$_2$ | 1.0 | 1 | 3 | 5–6 | |
| | (b) | Product Ex 12 | 1.0 | 0 | 0 | 2–3 | |
| | (c) | Product Ex 12 | 0.8 | 0 | 0 | 2–3 | |
| | (d) | Product Ex 12 | 0.6 | 0 | 0 | 4 | |
| | (e) | Product Ex 12 | 0.4 | 0 | 0 | >7 | |

Symbols are as follows

| | |
|---|---|
| A | represents monobutyltin tri iso-octyl thioglycollate |
| * | represents 0.5 parts of lubricant |
| ( ) | denotes wt. percentage |
| DBT(IOT)$_2$ | represents dibutyltin bis(iso-octyl thioglycollate) |
| DOT(IOT)$_2$ | represents dioctyltin bis(iso-octyl thioglycollate) |

We claim:

1. An organotin compound of the generic formula

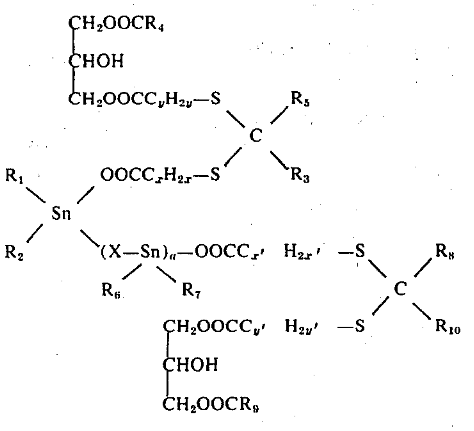

wherein

*a* is 0 or 1, each of *x*, *x'*, *y* and *y'*, which are the same or different, is an integer of 1–6, each of $R_1$, $R_2$, $R_6$ and $R_7$, which are the same or different is an alkyl group of 1 to 12 carbon atoms, a cycloalkyl group, an aromatic hydrocarbyl group or an aralkyl hydrocarbyl group, each of $R_4$ and $R_9$, which are the same or different, is as defined above for $R_1$, $R_2$, $R_6$ and $R_7$ or is an alkyl group of 13–21 carbon atoms, an alkenyl group of 2 to 21 carbon atoms, each of $R_5$ and $R_{10}$, which are the same or different, is as defined above for $R_4$ and $R_9$ or is hydrogen, each of $R_3$ and $R_8$ is as defined for $R_4$ and $R_9$ or is a substituted phenyl group with at least one substituent which is an alkyl group of 1 to 6 carbon atoms, an alkoxy group of 1 to 6 carbon atoms or a hydroxy group, or at least one of the pairs $R_3$ and $R_5$ and $R_8$ and $R_{10}$, together with the carbon atom to which they are attached, forms a cycloalkyl ring and X is oxygen or sulfur.

2. A compound according to claim 1 of the general formula

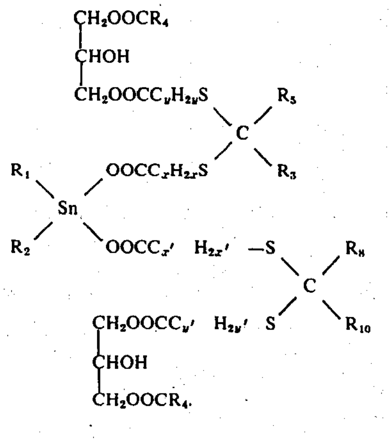

3. A compound according to claim 1 of the general formula

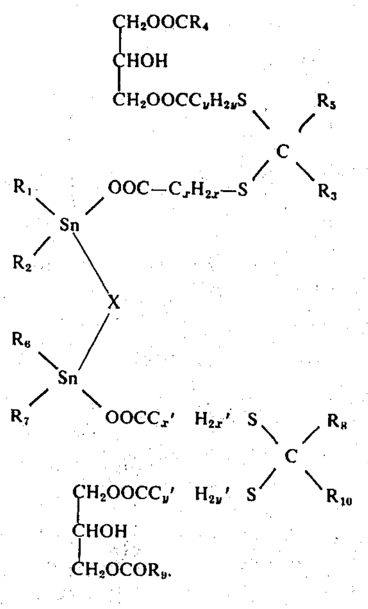

4. A compound according to claim 1 wherein each of *x*, *x'*, *y* and *y'* is 1 or 2.

5. A compound according to claim 1 wherein $R_1$, $R_2$, $R_3$, $R_4$, $R_5$, *x* and *y* are the same respectively as $R_6$, $R_7$, $R_8$, $R_9$, $R_{10}$, *x'* and *y'*.

6. A compound according to claim 1 wherein each of $R_1$, $R_2$, $R_6$ and $R_7$ is an alkyl group of 4–8 carbon atoms or a cycloalkyl group of 5–7 carbon atoms.

7. A compound according to claim 1 wherein each of $R_5$ and $R_{10}$ is hydrogen or an alkyl group of 1–6 carbon atoms.

8. A compound according to claim 1 wherein each of $R_4$ and $R_9$ is an alkyl group of 10–19 carbon atoms or an alkenyl group of 10–19 carbon atoms.

9. A compound according to claim 1 wherein each of $R_3$ and $R_8$ is a phenyl group; a branched chain alkyl group of 3–10 carbon atoms or a straight chain alkyl group of 7 to 13 carbon atoms.

10. A compound according to claim 9 wherein the groups

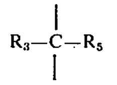

and

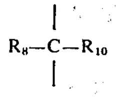

are the same and represent groups of formula

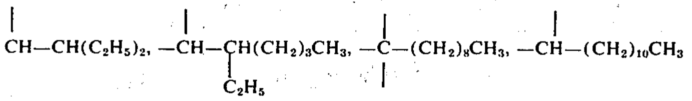

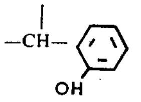

or

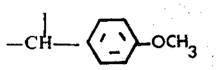

11. A compound according to claim 1 of the general formula

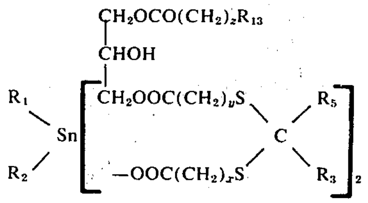

wherein each of $R_3$ and $R_{13}$, which are the same or different, is an alkyl group of 1 to 13 carbon atoms, a cycloalkyl group, an aryl or aralkyl group, $R_5$ is hydrogen, an alkyl or an aryl group, and *z* is an integer of 1 to 20.

12. A compound according to claim 11 wherein $R_{13}$ is a methyl group, $R_5$ is hydrogen or a methyl group and $R_3$ is a phenyl group, a branched chain alkyl group of 4 to 8 carbon atoms, or a straight chain alkyl group of 7 to 13 carbon atoms.

13. A compound according to claim 12 wherein $R_3$ is a phenyl, o-hydroxyphenyl, p-methoxyphenyl, hept-3-yl, pent-3-yl, n-nonyl or n-undecyl group, *z* is 16, $R_1$ and $R_2$ are n-butyl or n-octyl groups and *x* and *y* are 1 or 2.

14. A compound according to claim 3 wherein $R_1$, $R_2$, $R_6$ and $R_7$ are the same and are n-butyl or n-octyl groups, $R_3$ and $R_8$ are the same and are phenyl, o-hydroxyphenyl, p-methoxyphenyl, hept-3-yl, pent-3-yl, n-nonyl or n-undecyl groups, $R_4$ and $R_9$ are n-heptadecyl groups, $R_5$ and $R_{10}$ are the same and are hydrogen or methyl, *x*, *x'*, *y* and *y'* are the same and are 1 or 2, and X is oxygen or sulphur.

15. A compound according to claim 1 of the formula

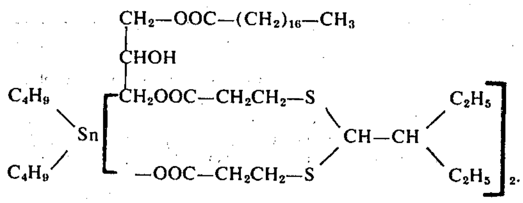

16. A compound according to claim 1 of the formula

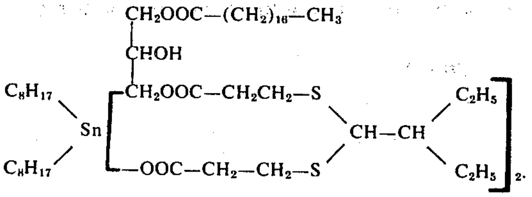

17. A compound according to claim 1 of the formula

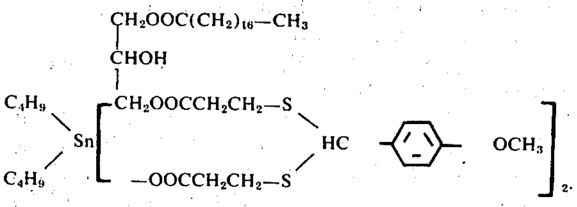

18. A compound according to claim 1 of the formula

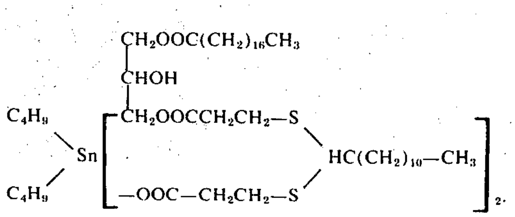

19. A compound according to claim 1 of the formula
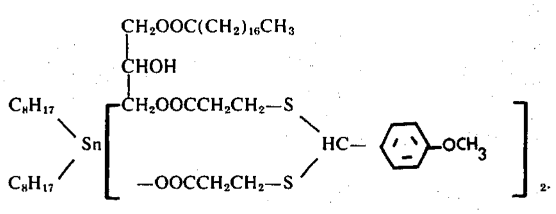
20. A compound according to claim 1 of the formula
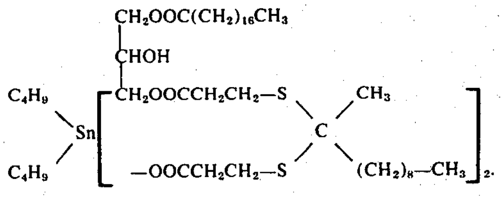
21. A compound according to claim 1 of the formula
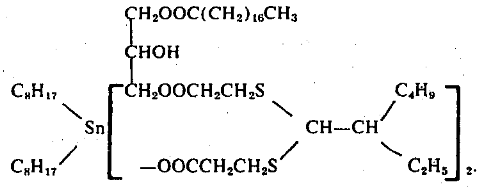
22. A compound according to claim 1 of the formula
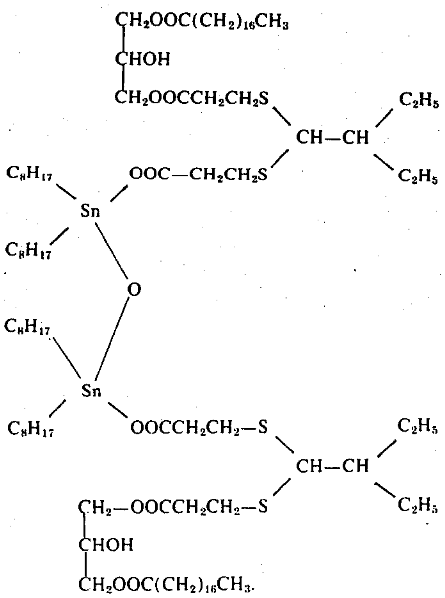
23. A compound according to claim 1 of the formula
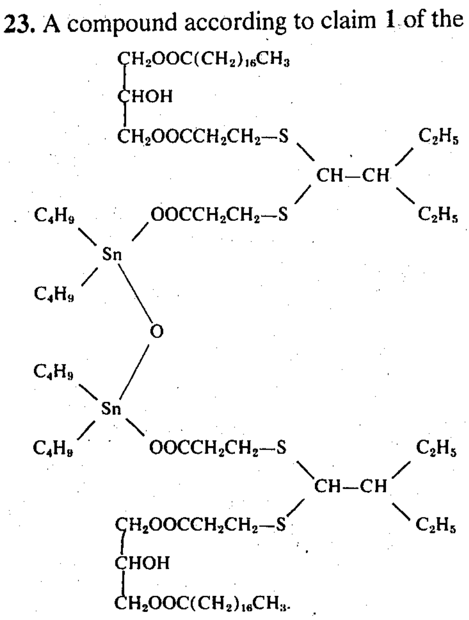
24. A compound according to claim 1 of the formula
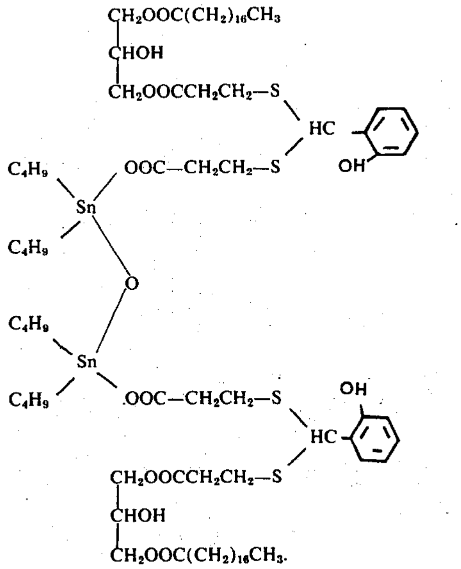
25. A compound according to claim 1 of the formula
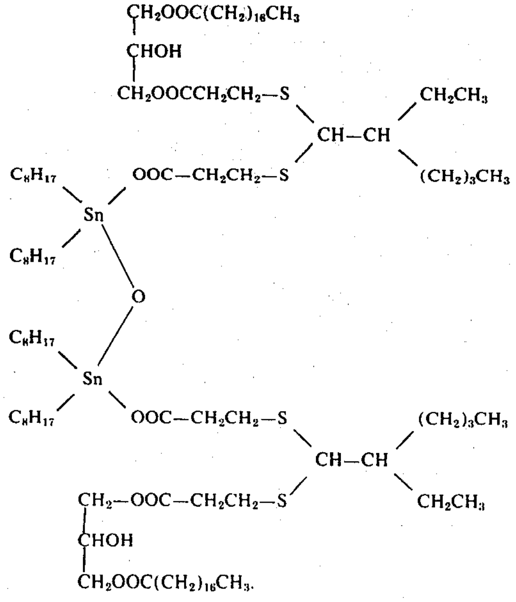

26. A compound according to claim 1 of the formula
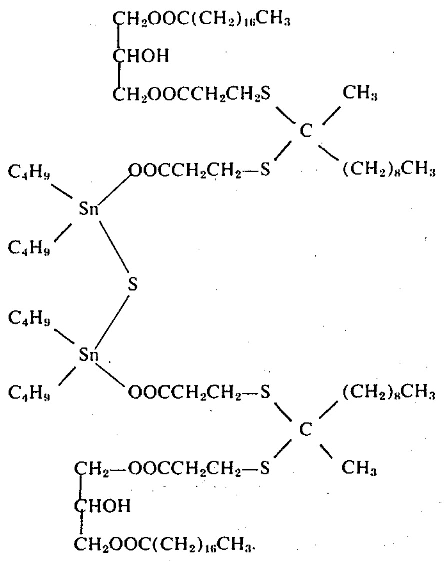
* * * * *

UNITED STATES PATENT OFFICE
CERTIFICATE OF CORRECTION

Patent No. 3,972,908 Dated August 3, 1976

Inventor(s) JOHN DESMOND COLLINS et al

It is certified that error appears in the above-identified patent and that said Letters Patent are hereby corrected as shown below:

Column 1, line 39, that portion of the formula reading $C_y H_{2y}$ should read $C_{y'} H_{2y'}$ .

Column 4, last line, that portion of the formula reading $(CH_2)$hd-x should read $(CH_2)_x$ .

Column 5, line 41, that portion of the formula reading s should read S .

Column 5, lines 64-67, that portion of the formula reading

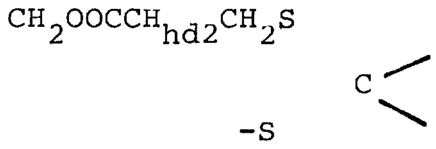

should read

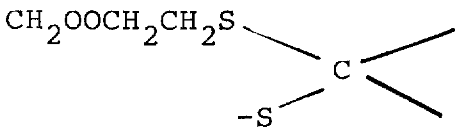

.

UNITED STATES PATENT OFFICE
CERTIFICATE OF CORRECTION

Patent No. 3,972,908     Dated August 3, 1976

Inventor(s) JOHN DESMOND COLLINS et al

It is certified that error appears in the above-identified patent and that said Letters Patent are hereby corrected as shown below:

Column 7, line 39, that portion of the formula reading $OOCCH_2CH_2-$ should read $OOCCH_2CH_2-$ .

Column 8, line 24, delete (first occurrence) "butylphenol".

Column 10, line 29, that portion of the formula reading $\underset{|}{C_2H_5}-CH-C_2H_5$ should read $C_2H_5-\underset{|}{CH}-C_2H_5$ .

Column 12, line 48, replace "hexanol" with --hexanal--.

Column 21, line 37, that portion of the formula reading $CH_2OOCH_2CH_2S$ should read $CH_2OOCCH_2CH_2S$ .

Signed and Sealed this

Fourth Day of April 1978

[SEAL]

Attest:

RUTH C. MASON
Attesting Officer

LUTRELLE F. PARKER
Acting Commissioner of Patents and Trademarks